(12) United States Patent
LeMaitre et al.

(10) Patent No.: US 6,333,970 B1
(45) Date of Patent: Dec. 25, 2001

(54) SINGLE-USE RADIOLOGICAL IMAGING AID

(75) Inventors: George W. LeMaitre, Charlestown; George D. LeMaitre, Andover, both of MA (US)

(73) Assignee: LeMaitre Vascular, Inc., Burling, MA (US)

( * ) Notice: Subject to any disclaimer, the term of this patent is extended or adjusted under 35 U.S.C. 154(b) by 0 days.

(21) Appl. No.: 09/633,323

(22) Filed: Aug. 7, 2000

(51) Int. Cl.⁷ .......................................... H05G 1/28
(52) U.S. Cl. ............................. 378/162; 378/163
(58) Field of Search ..................... 378/162, 163, 378/164, 165, 207

(56) References Cited

U.S. PATENT DOCUMENTS

| | | | |
|---|---|---|---|
| Re. 36,461 | * 12/1999 | Russell et al. ............... | 378/163 X |
| 2,650,308 | 8/1953 | Catlin ........................... | 250/59 |
| 4,506,676 | 3/1985 | Duska .......................... | 128/653 |
| 4,860,331 | 8/1989 | Williams et al. ............ | 378/163 |
| 5,052,035 | 9/1991 | Krupnick ..................... | 378/163 |
| 5,193,106 | * 3/1993 | DeSena ........................ | 378/163 |
| 5,216,700 | * 6/1993 | Cherian ....................... | 378/163 |

* cited by examiner

*Primary Examiner*—David P. Porta
(74) *Attorney, Agent, or Firm*—McDermott, Will & Emery

(57) ABSTRACT

A single-use radiological imaging aid includes an adhesive-backed tape and a backer covering the adhesive. Both the tape and the backer include radiopaque indicia. The indicia on the tape may include locating and/or measurement markings to identify, locate and/or measure anatomical features in a radiological image. The indicia on the backer includes alphanumeric and/or graphic symbols which define a blocking field. When the backer is intact over the adhesive surface of the tape, the blocking field on the backer is in substantial registration with the indicia on the tape. The backer must be removed prior to use of the tape in a radiological image, or else the blocking field will obscure the indicia on the tape in a scanned image. This design ensures that the tape will be properly adhered to a patient's skin prior to imaging and will be used only once.

8 Claims, 1 Drawing Sheet

SINGLE-USE RADIOLOGICAL IMAGING AID

TECHNICAL FIELD

This invention relates in general to radiological apparatus and in particular to a single-use imaging aid for use in x-ray and other imaging procedures.

BACKGROUND OF THE INVENTION

In the taking of medical x-rays, it is common to utilize a radiopaque marker on a portion of the patient's body being examined. One simple technique is to place the radiopaque marker on the patient's nipple when the x-ray is taken and the resulting mark on the x-ray film provides a point of reference from which actual measurements can be made to other parts of the body for surgical or other purposes. Other more complicated devices involving grids of radiopaque material carried by plastic sheets or lattice works of radiopaque rods have also been used in an effort to locate precisely the area of the body which is under investigation. Unquestionably, some of these devices have achieved some acceptance as aids in the preparation for specific surgical procedures. However, the available devices have tended to be expensive, complicated, and difficult to use. By way of example, one of the devices on the market involves a contoured carrier which is strapped to the patient's body and on which a movable radiopaque indicator slides. Thumbscrews are provided to lock the indicator in any desired position prior to the taking of the x-ray.

Another prior art device involves the placement of radiosensitive film under the patient's body and applying a carrier sheet on which grid lines of radiopaque material are disposed over a portion of the body. When the film is exposed to radiation passing through the carrier sheet and the patient's body, an image is developed in which the grid lines appear. Openings are provided in the device to permit the radiologist to make visible markings on the patient's body as points of reference. Both of the systems described are expensive, unwieldy and somewhat imprecise. Moreover, they are useful only for a few limited applications.

In addition, for hygienic reasons, it is important that such devices be sterile when applied to a patient's skin, be reliably adherable to the patient's skin, yet removable without leaving traces of adhesive or irritating the patient's skin, and be usable only one time on a patient.

SUMMARY OF THE INVENTION

According to one aspect of the invention, there is provided a single-use radiological imaging aid which is removably applicable to a body part so that the body part and the aid are visible in an x-ray or other radiological image. The aid comprises a flexible, imperforate, radiation-transparent tape having first and second surfaces, radiopaque indicia formed on one of the first and second surfaces of the tape by selective application of a radiopaque material thereon, an adhesive on the other of the first and second surfaces of the tape for removable attachment of the tape to the skin of the body part, and a removable backer removably disposed over the adhesive. The backer includes a radiopaque blocking field formed thereon by selective application of a radiopaque material on the backer. When the backer is in place over the adhesive, the blocking field on the backer is in substantial registration with the indicia on the tape. The indicia on the tape are visible in a radiological image of the body part upon removal of the backer from the tape and adherence of the tape to the skin of the body part prior to imaging of the body part. A radiological image of the tape with the backer in place would reveal only the blocking field and not the indicia on the tape.

In a preferred embodiment, the blocking field on the backer comprises radiopaque indicia in the form of graphic or alphanumeric symbols which are preferably arranged in irregular nonrepeating patterns.

The indicia on one or both of the tape and backer may be covered with a protective coating or layer. In a preferred embodiment, the protective coating is substantially inert and substantially transparent to x-radiation.

At least one of the tape and the backer preferably comprises a nonwoven material.

The radiopaque indicia on the tape may include locating markings and/or linear measurement graduations which represent units of conventional linear measurement.

BRIEF DESCRIPTION OF THE DRAWINGS

For a better understanding of the present invention, together with other objects, features, and advantages, reference should be made to the following description of a preferred embodiment, which should be read with reference to the appended drawings, in which.

Like elements in the FIGURES are indicated by like reference numerals.

DETAILED DESCRIPTION OF THE DRAWINGS

Figure 1:
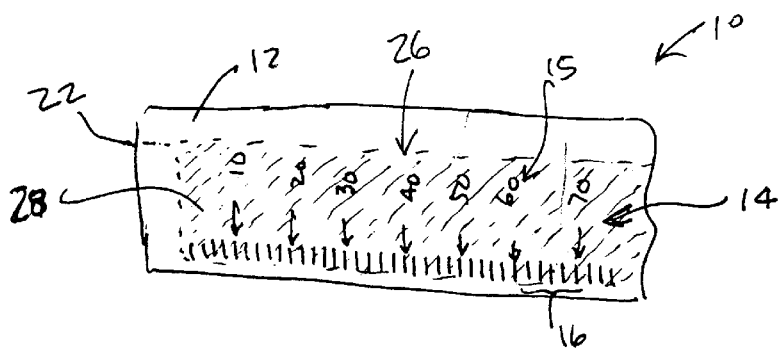
FIG. 1 is an elevational view of one form of a radiological imaging aid made in accordance with the present invention.

The radiological imaging aid of the present invention is designed to ensure that it is used only one time on a patient and is properly adhered to the patient's skin prior to and during a radiological scan. It is preferably constructed as a pliable, imperforate, nonwoven tape material which includes radiopaque indicia formed on one surface and an adhesive on the opposite surface. The adhesive is preferably covered and protected with a removable backer so that the tape can be conveniently stored and transported prior to use without inadvertent adherence to itself or other objects.

According to the invention, the removable backer covering the adhesive also includes radiopaque indicia which define a blocking field. When the backer is present over the adhesive surface of the tape, the blocking field is in substantial registration with the indicia on the tape. When the backer is removed from the tape and the tape is applied to a patient's skin to identify or locate a region of interest, the blocking field is also removed, and the indicia on the tape can be clearly viewed in the resulting image. This design ensures that the tape will be adhered to the patient's skin and not merely laid over the body part. If the backer is intact over the adhesive, the blocking indicia in the backer will obscure the indicia on the tape in any scanned image of the patient in which the imaging aid is used. The aid is therefore not useful unless the backer is removed from the tape and the tape is adhered to the patient's skin. This ensures that the patient is always contacted with a sterile imaging aid which has not previously been applied to another patient or to more than one location on a patient. If x-ray images of multiple regions of the patient are desired, multiple aids according to the invention can be adhered to the patient simultaneously, thereby reducing overall radiation exposure and pre-imaging labor.

The imaging aid of the present invention may be of any convenient length. The indicia on the tape may include locating markings and/or linear measurement markings or graduations which represent conventional measuring units in, for example, the metric or English systems, or both.

The tape may be made from any one of a number of pliable materials. Among those available commercially is a nonwoven medical tape made of, for example, white rayon fabric having an acrylic binder. One surface of the tape is preferably coated with an adhesive which may desirably be, for example, hypo-allergenic for maximum patient comfort, and pressure-sensitive for ease of use. The backer may include, for example, a release paper treated with silicone or the like.

The indicia on the tape and the backer are preferably formed and applied by techniques such as, for example, screen printing, dipping, deposition or dispensing. The material used is in the form of an ink suspension, the primary requirement for which is radiopacity. Perhaps the best of available materials is a slurry of a plastisol carrier and fine lead particles, although other materials are quite satisfactory in some instances, depending upon various factors. These may include the desired length of exposure to radiation, the particular area or body part under examination, its location in the body, and the like. Some useful radiopaque materials include slurries of particles of barium, triphenylbismuth, tantalum or aluminum. The radiopaque indicia may be coated with a protective coating or layer of a radiation-transparent material if desired.

Figure 2:
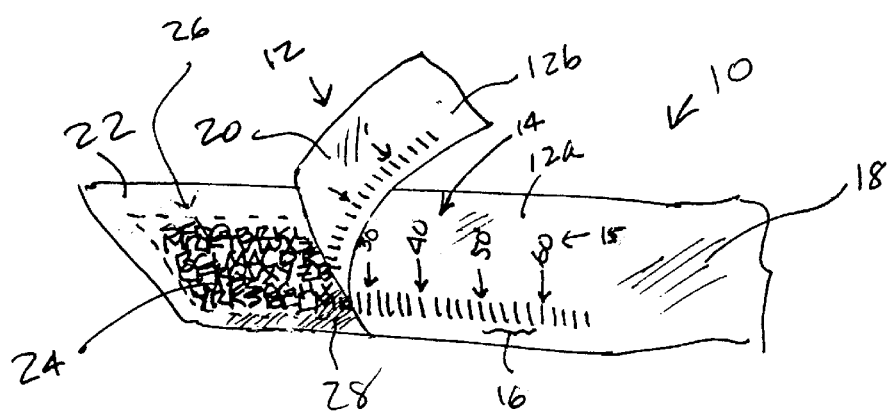
FIG. 2 is a perspective view showing the construction of the aid of FIG. 1.

As shown in FIGS. 1 and 2, the imaging aid 10 of the present invention comprises a flexible tape 12 having first surface 12a and second surface 12b. On the first surface 12a are printed indicia 14 in a radiopaque ink or similar material suitable for dispensing onto the tape 12. The indicia may include, for example alphanumeric or other symbols 15 and graduated markings 16, if desired. An optional radiation-transparent coating or layer 18 may be disposed over the indicia 14.

The second surface 12b of the tape 12 includes an adhesive 20. A removable backer 22 is disposed over the adhesive. The backer 22 itself contains radiopaque indicia 24 arranged to define a blocking field 26 which is in substantial registration with the indicia 14 on the tape when the backer 22 is in place over the adhesive 20 on the tape 12. The blocking indicia 24 may optionally be coated with a radiation-transparent coating or covering 28.

Placement of the aid 10 on a portion of a patient's body (not shown) in preparation for a radiological scan is accomplished by removing the backer 22 from the tape 12 so as to expose the adhesive 20 on the second surface 12b. The tape 12 is adhered to the patient's body at a region of interest, and the region of interest is then scanned with x-rays or other imaging energy. The resulting image will clearly display the indicia 14 and other anatomical features identified and/or located with the aid.

Figure 3A:
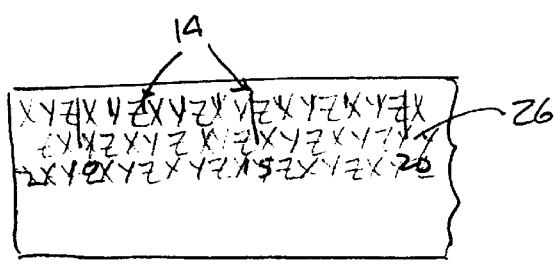
FIGS. 3A–3C show the effect of different blocking field densities in radiological images using the aid of FIGS. 1 and 2.
Figure 3B:
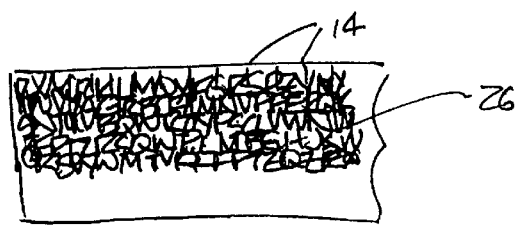
Figure 3C:
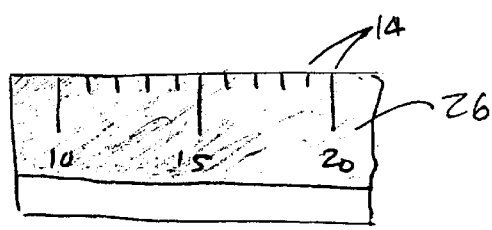

The indicia 24 defining the blocking field have several novel and important features which must be present for accomplishment of the desired objectives. First, the blocking field 26 is preferably comprised of many discrete indicia, such as graphic or alphanumeric symbols, as illustrated in FIGS. 3A and 3B, instead of a uniformly opaque field, as illustrated in FIG. 3C. A disadvantage of a uniformly opaque field, as in FIG. 3C, is that the indicia 14 on the tape 12 may be visible through a uniformly opaque blocking field 26 if the indicia 14 on the tape 12 are sufficiently dense. To prevent this occurrence, a uniformly opaque blocking field would need to be as dense as, or preferably denser than, the indicia 14 on the tape 12, and this would be time-consuming, labor-intensive, and costly to accomplish.

In contrast, if discrete graphic or alphanumeric symbols are used as the indicia 24 in the blocking field 26 on the backer 22, a portion of the blocking field is free of radiopaque ink, as clearly shown in FIGS. 3A and 3B. The presence and absence of radiopaque ink in irregular patterns in the blocking field 26 enhances the blocking field's ability to obscure or block the legibility of any superimposed indicia, such as indicia 14 on the tape 12, unless the backer 22 is removed from the tape and the tape adhered to the patient.

It will be noted that the blocking field 26 in FIG. 3B, although comprised of alphanumeric symbols as described above, is less dense than that of FIG. 3C and therefore offers a lesser degree of blocking. The indicia 14 on the tape 12 can be seen through the blocking field 26.

Second, the blocking indicia 24 are preferably arranged in nonrepeating irregular patterns, as shown in FIG. 3B. The patterns may overlap to some degree. Such an arrangement offers maximum obscuring of the indicia 14 on the tape 12 while using a minimum quantity and density of ink and reduces manufacturing time, labor and expense.

Because certain changes may be made in the above apparatus without departing from the scope of the invention herein disclosed, it is intended that all matter contained in the above description or shown in the accompanying drawings shall be interpreted in an illustrative and not a limiting sense.

We claim:

1. A single-use radiological imaging aid applicable to a body part, the device comprising:
    a flexible, imperforate, radiation-transparent tape having first and second surfaces;
    radiopaque indicia formed on one of the first and second surfaces of the tape by selective application of a radiopaque material thereon;
    a radiation transparent adhesive on the other of the first and second surfaces of the tape for removable attachment of the tape to the skin of the body part; and
    a removable backer removably disposed over the adhesive, the backer including a radiopaque blocking field formed thereon by selective application of a radiopaque material, wherein the blocking field is in substantial registration with the indicia on the tape when the backer is adhered to the adhesive on the tape,
    wherein the indicia on the tape are visible in a radiological image of the body part upon removal of the backer from the tape and adherence of the tape to the skin of the body part prior to a radiological scan of the body part.

2. A single-use radiological imaging aid according to claim 1, wherein the blocking field comprises radiopaque indicia.

3. A single-use radiological imaging aid according to claim 2, wherein the radiopaque indicia in the blocking field comprise graphic and/or alphanumeric symbols.

4. A single-use radiological imaging aid according to claim 3, wherein the radiopaque indicia on the backer are arranged in irregular nonrepeating patterns.

5. A single-use radiological imaging aid according to claim 1, wherein a protective layer is disposed over the radiopaque indicia on at least one of the tape and the backer.

6. A single-use radiological imaging aid according to claim 5, wherein the protective layer is substantially inert and substantially transparent to x-radiation.

7. A single-use radiological imaging aid according to claim 1, wherein at least one of the tape and the backer comprises a nonwoven material.

8. A single-use radiological imaging aid according to claim 1, wherein the indicia on the tape comprise locating markings and/or linear measurement graduations representing conventional units of linear measurement.

* * * * *